(12) United States Patent
Ikeda et al.

(10) Patent No.: US 9,220,397 B2
(45) Date of Patent: Dec. 29, 2015

(54) ENDOSCOPE

(75) Inventors: Toshiyuki Ikeda, Kanagawa (JP); Kan Naito, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 487 days.

(21) Appl. No.: 13/158,102

(22) Filed: Jun. 10, 2011

(65) Prior Publication Data

US 2011/0306837 A1    Dec. 15, 2011

(30) Foreign Application Priority Data

Jun. 11, 2010   (JP) .................................. 2010-134015

(51) Int. Cl.

| A61B 1/06 | (2006.01) |
|---|---|
| A61B 1/04 | (2006.01) |
| A61B 1/00 | (2006.01) |
| A61B 1/12 | (2006.01) |

(52) U.S. Cl.
CPC ........... *A61B 1/00091* (2013.01); *A61B 1/0008* (2013.01); *A61B 1/126* (2013.01)

(58) Field of Classification Search
USPC ......... 600/104, 106, 107, 109–113, 121–125, 600/127–130, 153–182
See application file for complete search history.

(56) References Cited

U.S. PATENT DOCUMENTS

| 5,871,440 A | 2/1999 | Okada ........................... 600/129 |
|---|---|---|
| 2006/0229497 A1 | 10/2006 | Toyama ......................... 600/156 |
| 2007/0260118 A1 | 11/2007 | Otawara ......................... 600/129 |
| 2008/0086032 A1 | 4/2008 | Ichimura ....................... 600/156 |
| 2009/0253966 A1 | 10/2009 | Ichimura ....................... 600/175 |

FOREIGN PATENT DOCUMENTS

| AU | 2006245250 B2 | 11/2006 | | |
|---|---|---|---|---|
| EP | 1 692 995 A1 | 8/2006 | | |
| EP | 1 880 656 A1 | 1/2008 | | |
| EP | 1 908 392 A1 | 4/2008 | | |
| JP | 10-309259 A | 11/1998 | | |
| JP | 11239563 A | * 9/1999 | ............... | A61B 1/00 |
| JP | 2004-254729 A | 9/2004 | | |
| JP | 2005-168770 A | 6/2005 | | |
| JP | 2006-314459 A | 11/2006 | | |

(Continued)

OTHER PUBLICATIONS

European Office Action dated Oct. 24, 2011.

(Continued)

*Primary Examiner* — Ryan Henderson
(74) *Attorney, Agent, or Firm* — McGinn IP Law Group PLLC

(57) ABSTRACT

Provided is an endoscope which is capable of preventing liquid drops from attaching onto the vicinity of an observation window even in the case where the observation window is placed in the vicinity of a round-chamfered peripheral edge part. In the case where an observation window is placed in the vicinity of a round-chamfered peripheral edge part, the peripheral edge part in the vicinity of the observation window is round-chamfered in a manner that the radius of curvature (round-chamfer) becomes larger along with an increase in distance from a starting point, the starting point being the point closest to the observation window. With this feature, it is possible to prevent the liquid drops from attaching onto the vicinity of the observation window to thereby block the field of view.

5 Claims, 9 Drawing Sheets

(56) References Cited

FOREIGN PATENT DOCUMENTS

| | | |
|---|---|---|
| JP | 2006-320366 A | 11/2006 |
| JP | 2006-320367 A | 11/2006 |
| JP | 2007-202836 A | 8/2007 |
| JP | 2007-209395 A | 8/2007 |
| JP | 2008-86664 A | 4/2008 |
| WO | WO 2005/055816 A1 | 6/2005 |
| WO | WO 2006/120797 A1 | 11/2006 |

OTHER PUBLICATIONS

Chinese Office Action dated May 30, 2014 with English translation.

* cited by examiner

ENDOSCOPE

BACKGROUND OF THE INVENTION

1. Field of the Invention

The presently disclosed subject matter relates to an endoscope, and more particularly, to an endoscope in which an observation window can be cleaned by jetting a cleaning fluid from a nozzle.

2. Description of the Related Art

In general, an endoscope for medical use is provided with a nozzle for cleaning an observation window, and the observation window can be cleaned as needed by jetting a cleaning liquid from the nozzle.

However, when the observation window is cleaned by jetting the cleaning liquid from the nozzle in this way, the cleaning liquid attaches onto the observation window to block the field of view of the observation window in some cases. Therefore, in the endoscope for medical use, the cleaning liquid and air can be selectively jetted from the nozzle, and the air is jetted after the cleaning liquid is jetted, whereby the cleaning liquid attaching on the observation window can be blown away by the air to be removed.

However, the air is jetted only in a given direction, and hence the air does not reach the cleaning liquid depending on an attachment position of the cleaning liquid, so that the cleaning liquid cannot be completely removed in some cases.

Japanese Patent Application Laid-Open No. 2007-202836 describes that, in order to let the cleaning liquid drain off to a higher level, a suction port is placed in the vicinity of an observation window farther from the nozzle, of two observation windows.

In addition, Japanese Patent Application Laid-Open No. 2005-168770 describes that an illumination window is formed so as to be inclined in a manner that an optical axis of an illumination optical system is inclined.

Further, Japanese Patent Application Laid-Open No. 2004-254729 describes an endoscope including a distal end part to which a cap is detachably attached, in which a joining portion between an end part of the cap and an end part of a distal end part main body is formed so as to have a continuous curved surface.

In addition, Japanese Patent Application Laid-Open Nos. 2006-314459, 2006-320366, 2006-320367, and 2008-86664 each describe that an end surface of the distal end part on which the observation window is placed is formed in a stepwise manner, an inclined surface is formed in a wall part between respective adjacent two steps, and the cleaning liquid is jetted from the cleaning nozzle toward the inclined surfaces.

SUMMARY OF THE INVENTION

Incidentally, in recent years, a diameter of the endoscope for medical use becomes increasingly smaller, in a manner that the observation window needs to be placed in the vicinity of a peripheral edge part of the distal end surface in some cases.

However, normally, in order to reduce a stimulus when a distal end surface of an insertion part of the endoscope comes into contact with a body cavity wall, a peripheral edge part of the distal end surface is round-chamfered, and there are problems that drops of the cleaning liquid and the like attach easily onto such a round-chamfered portion, and that it is difficult to remove the liquid drops once attaching thereon.

The presently disclosed subject matter has been made in view of the above-mentioned circumstances, and therefore has an object to provide an endoscope which is capable of preventing liquid drops from attaching onto the vicinity of an observation window even in the case where the observation window is placed in the vicinity of a round-chamfered peripheral edge part.

In order to achieve the above-mentioned object, a first aspect of the presently disclosed subject matter provides an endoscope including: an insertion part which is inserted into a body cavity, the insertion part having a distal end surface whose peripheral edge part is circumferentially round-chamfered; an observation window placed on the distal end surface; an illumination window placed on the distal end surface; and a nozzle which jets a cleaning fluid toward the observation window, wherein: the observation window is placed in a vicinity of the peripheral edge part; and in a vicinity of the observation window, the peripheral edge part is round-chamfered in a manner that a radius of round-chamfer becomes larger along with an increase in distance from a starting point which is a point closest to the observation window.

According to the first aspect, in the case where the observation window is placed in the vicinity of the round-chamfered peripheral edge part, the peripheral edge part in the vicinity of the observation window is round-chamfered in a manner that the radius of curvature becomes larger along with an increase in distance from the starting point, the starting point being the point closest to the observation window. It is confirmed that, in the case where the peripheral edge part is round-chamfered, drops of the cleaning fluid and the like attach more easily onto the round-chamfered portion, and tend to attach particularly easily onto a portion having a larger radius of curvature in the round-chamfered peripheral edge part. In view of the above, the peripheral edge part in the vicinity of the observation window is round-chamfered in a manner that the radius of curvature becomes larger along with an increase in distance from the starting point, the starting point being the point closest to the observation window, whereby the liquid drops are prevented from attaching onto the peripheral edge part near the observation window (the liquid drops are led so as to attach at a position away from the observation window). With this feature, it is possible to prevent the liquid drops from attaching onto the vicinity of the observation window to thereby block the field of view.

It should be noted that a mode of changing the radius of curvature (round-chamfer) is not limited, and hence the radius of curvature may be changed continuously from the starting point, or may be changed in a stepwise manner from the starting point. In addition, a change rate of the radius of curvature does not necessarily need to be constant, and may be changed drastically with respect to a certain point as the starting point. For example, it is also possible to adopt a mode in which: the point closest to the observation window is defined as the starting point; and the distal end part is round-chamfered at the same radius of curvature as that at the starting point within a given range from the starting point, and is round-chamfered at the radius of curvature which is changed continuously or in a stepwise manner, once exceeding the given range.

In order to achieve the above-mentioned object, a second aspect of the presently disclosed subject matter provides the endoscope according to the first aspect in which: the illumination window is placed in a vicinity of the peripheral edge part; and in a vicinity of the illumination window, the peripheral edge part is round-chamfered in a manner that the radius of curvature becomes larger along with an increase in distance from a starting point which is a point closest to the illumination window.

According to the second aspect, in the case where the illumination window is placed in the vicinity of the round-chamfered peripheral edge part (including the case where a plurality of the illumination windows are placed), the peripheral edge part in the vicinity of the illumination window is round-chamfered in a manner that the radius of curvature (round-chamfer) becomes larger along with an increase in distance from the starting point which is the point closest to the illumination window. With this feature, it is possible to prevent the liquid drops from attaching onto the vicinity of the illumination window to thereby deteriorate illumination performance.

In order to achieve the above-mentioned object, a third aspect of the presently disclosed subject matter provides an endoscope including: an insertion part which is inserted into a body cavity, the insertion part having a distal end surface whose peripheral edge part is circumferentially round-chamfered; an observation window placed on the distal end surface; an illumination window placed on the distal end surface; and a nozzle which jets a cleaning fluid toward the observation window, wherein: the observation window and the illumination window are placed adjacently to each other in a vicinity of the peripheral edge part; and within a range between a first point being a point closest to the observation window and a second point being a point closest to the illumination window, the peripheral edge part is round-chamfered in a manner that a radius of round-chamfer gradually becomes larger from each of the first point and the second point toward a given local maximum point which is set between the first point and the second point.

According to the third aspect, in the case where the observation window and the illumination window are placed adjacently to each other in the vicinity of the round-chamfered peripheral edge part, the peripheral edge part between the observation window and the illumination window is round-chamfered in a manner that the radius of curvature becomes larger toward the given local maximum point set between the observation window and the illumination window. With this feature, it is possible to lead the liquid drops to a position away from the observation window and the illumination window and to prevent the liquid drops from attaching onto the vicinities of the observation window and the illumination window.

In order to achieve the above-mentioned object, a fourth aspect of the presently disclosed subject matter provides the endoscope according to the third aspect, in which a pair of the illumination windows is placed on the distal end surface so as to sandwich the observation window.

According to the fourth aspect, the observation window is placed in the vicinity of the round-chamfered peripheral edge part, and the pair of illumination windows is placed adjacently to the observation window so as to sandwich the observation window. In this case, the peripheral edge part between the observation window and each of the illumination windows is round-chamfered in a manner that the radius of curvature becomes larger toward the given local maximum point set between the observation window and each of the illumination windows. With this feature, it is possible to lead the liquid drops to a position away from the observation window and the illumination window and to prevent the liquid drops from attaching onto the vicinities of the observation window and the illumination window.

In order to achieve the above-mentioned object, a fifth aspect of the presently disclosed subject matter provides the endoscope according to the third or fourth aspect, in which the local maximum point is set at a substantially middle (intermediate) position between the first point and the second point.

According to the fifth aspect, the local maximum point is set at the substantially middle position between the first point (the point closest to the observation window) and the second point (the point closest to the illumination window). With this feature, it is possible to smoothly change the radius of curvature and to lead the liquid drops to a position away from both of the observation window and the illumination window.

In order to achieve the above-mentioned object, a sixth aspect of the presently disclosed subject matter provides an endoscope including: an insertion part which is inserted into a body cavity, the insertion part having a distal end surface whose peripheral edge part is circumferentially round-chamfered; an observation window placed on the distal end surface; an illumination window placed on the distal end surface; and a nozzle which jets a cleaning fluid toward the observation window, wherein: the observation window is placed in a vicinity of the peripheral edge part; and within a range between a first point being a point closest to the observation window and a second point apart from the first point by a given distance, the peripheral edge part is round-chamfered in a manner that a radius of round-chamfer gradually becomes larger from each of the first point and the second point toward a given local maximum point which is set between the first point and the second point.

According to the sixth aspect, in the case where the observation window is placed in the vicinity of the round-chamfered peripheral edge part, within the range between the first point being the point closest to the observation window and the second point being the point away from the first point by the given distance, the peripheral edge part is round-chamfered in a manner that the radius of curvature gradually becomes larger toward the given local maximum point being set between the first point and the second point. With this feature, it is possible to lead the liquid drops to a position away from the observation window and to prevent the liquid drops from attaching onto the vicinity of the observation window.

In order to achieve the above-mentioned object, a seventh aspect of the presently disclosed subject matter provides the endoscope according to the sixth aspect, in which the local maximum point is set at a substantially middle (intermediate) position between the first point and the second point.

According to the seventh aspect, the local maximum point is set at the substantially middle (intermediate) position between the first point and the second point. With this feature, it is possible to smoothly change the radius of curvature.

In order to achieve the above-mentioned object, an eighth aspect of the presently disclosed subject matter provides the endoscope according to the sixth or seventh aspect, in which the second point is set in a direction away from the nozzle with respect to the first point.

According to the eighth aspect, the second point is set in a direction away from the nozzle with respect to the first point. That is, the second point is set on the downstream side of the cleaning fluid jetted from the nozzle. The force of the cleaning fluid becomes weaker on the downstream side, and hence the liquid drops attach more easily on the downstream side than on the upstream side. On such a downstream side, the liquid drops are led to a position away from the observation window, whereby it is possible to effectively prevent the liquid drops from attaching onto the vicinity of the observation window.

In order to achieve the above-mentioned object, a ninth aspect of the presently disclosed subject matter provides the endoscope according to the seventh or eighth aspect, in which: the illumination window is placed in a vicinity of the peripheral edge part adjacently to the observation window; and a point closest to the illumination window is defined as the second point.

According to the ninth aspect, the illumination window is placed in the vicinity of the peripheral edge part adjacently to the observation window, and the point closest to the illumination window is defined as the second point. With this feature, it is possible to prevent the liquid drops from attaching onto the vicinity of the illumination window.

In order to achieve the above-mentioned object, a tenth aspect of the presently disclosed subject matter provides the endoscope according to any one of the first to ninth aspects, in which the peripheral edge part is round-chamfered in a manner that the radius of curvature (round-chamfer) becomes the smallest at the point closest to the observation window.

According to the tenth aspect, the peripheral edge part is round-chamfered in a manner that the radius of curvature (round-chamfer) becomes the smallest at the point closest to the observation window. The liquid drops tend to attach more easily onto a portion having a larger radius of curvature, and hence the radius of curvature is made smaller at the point closest to the observation window, whereby it is possible to effectively prevent the liquid drops from attaching onto the vicinity of the observation window.

According to the presently disclosed subject matter, it is possible to prevent the liquid drops from attaching onto the vicinity of the observation window even in the case where the observation window is placed in the vicinity of the round-chamfered peripheral edge part.

DETAILED DESCRIPTION OF THE PREFERRED EMBODIMENTS

Hereinafter, preferred embodiments of an endoscope according to the presently disclosed subject matter are described in detail with reference to the attached drawings.

First Embodiment

Figure 1:
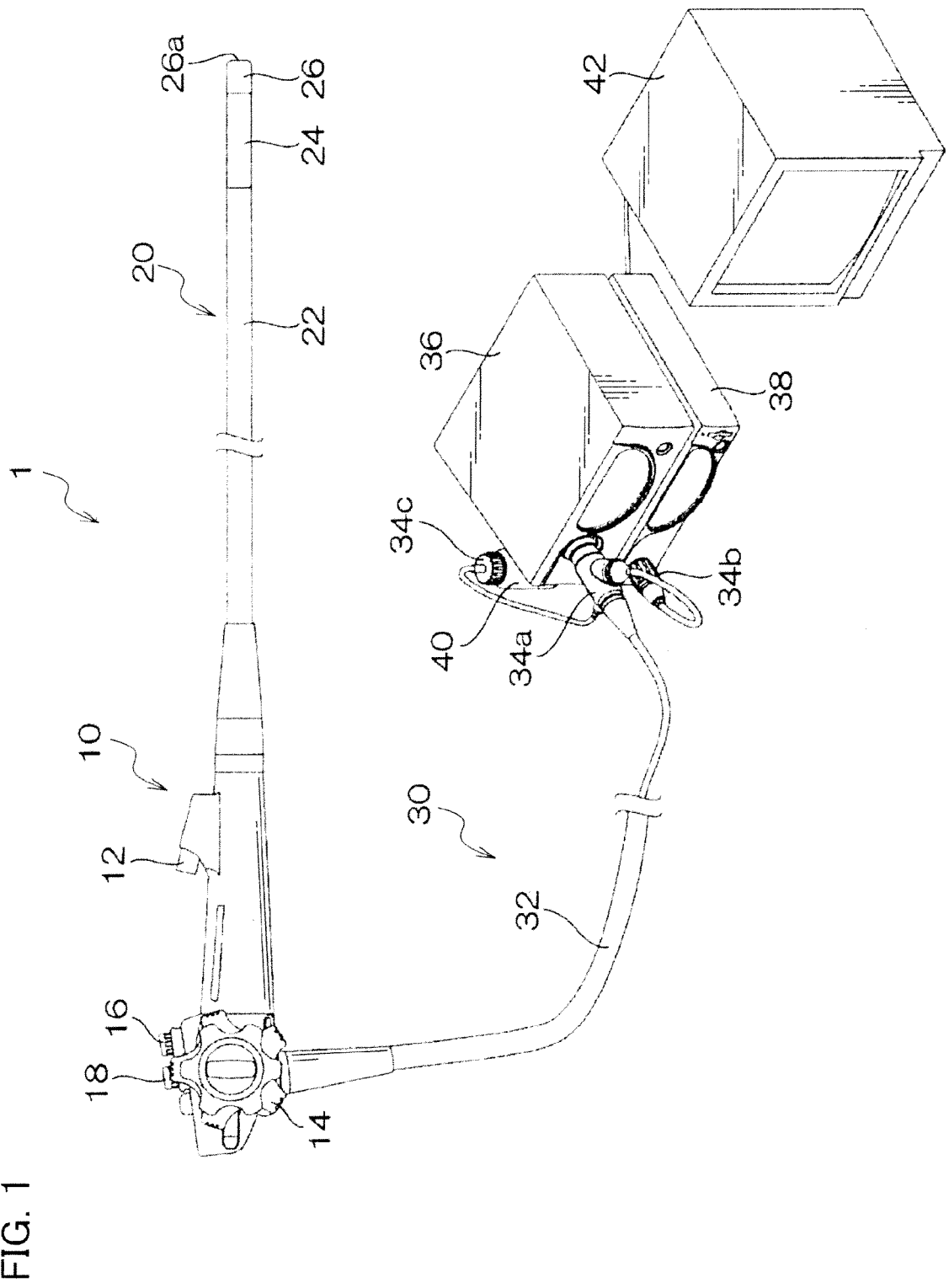
FIG. 1 is an overall configuration view illustrating an endoscope.

FIG. 1 is an overall configuration view illustrating an embodiment of the endoscope according to the presently disclosed subject matter.

An endoscope 1 is an electronic endoscope which takes out a subject image inside of a body cavity as an electronic image, and includes: an operation part 10 which is used by an operator in order to perform a required operation; an insertion part 20 which is inserted into the body cavity; and a connection part 30 for connecting with a processor apparatus and the like.

The connection part 30 includes: a universal cord 32 which is provided so as to be continuous with the operation part 10; and a plurality of connectors which are provided at a distal end part of the universal cord 32. These connectors includes: a processor connector 34A for connecting with a processor apparatus 36; a light source connector 34B for connecting with a light source apparatus 38; and an air supply/water supply connector 34C for connecting with an air supply/water supply apparatus 40.

The operation part 10 includes: a forceps entrance 12 for inserting a treatment tool; an angle knob 14 for bending a distal end of the insertion part 20 up, down, right, or left; an air supply/water supply button 16 for cleaning an observation window 50 provided at the distal end of the insertion part 20, by jetting water and air from a nozzle 58 provided at the distal end of the insertion part 20; and a suction button 18 for suctioning from a forceps exit 56 provided at the distal end of the insertion part 20.

The insertion part 20 is formed into a tube-like shape which has a given diameter and is circular in cross-section, and is integrally provided so as to be continuous with a distal end of the operation part 10. The insertion part 20 includes: a flexible part 22 having flexibility; a bending part 24 which is bendable and provided at an end of the flexible part 22; and a distal end part 26 provided at a distal end of the bending part 24.

The flexible part 22 is configured by a flexible tube, and is integrally provided so as to be continuous with the distal end of the operation part 10. A large part of the insertion part 20 is configured by the flexible part 22.

The bending part 24 is configured to be bendable, and is integrally provided so as to be continuous with a distal end of the flexible part 22. The bending part 24 bends up, down, right, or left so as to follow an operation on the angle knob 14 provided in the operation part 10. Accordingly, the distal end part 26 can be turned in a desired direction inside of the body cavity by bending the bending part 24 in the desired direction.

The distal end part 26 is formed into a columnar shape (having, for example, a diameter of approximately 9 mm) by using a hard material such as metal (for example, stainless), and is integrally provided so as to be continuous with the distal end of the bending part 24.

Figure 2:
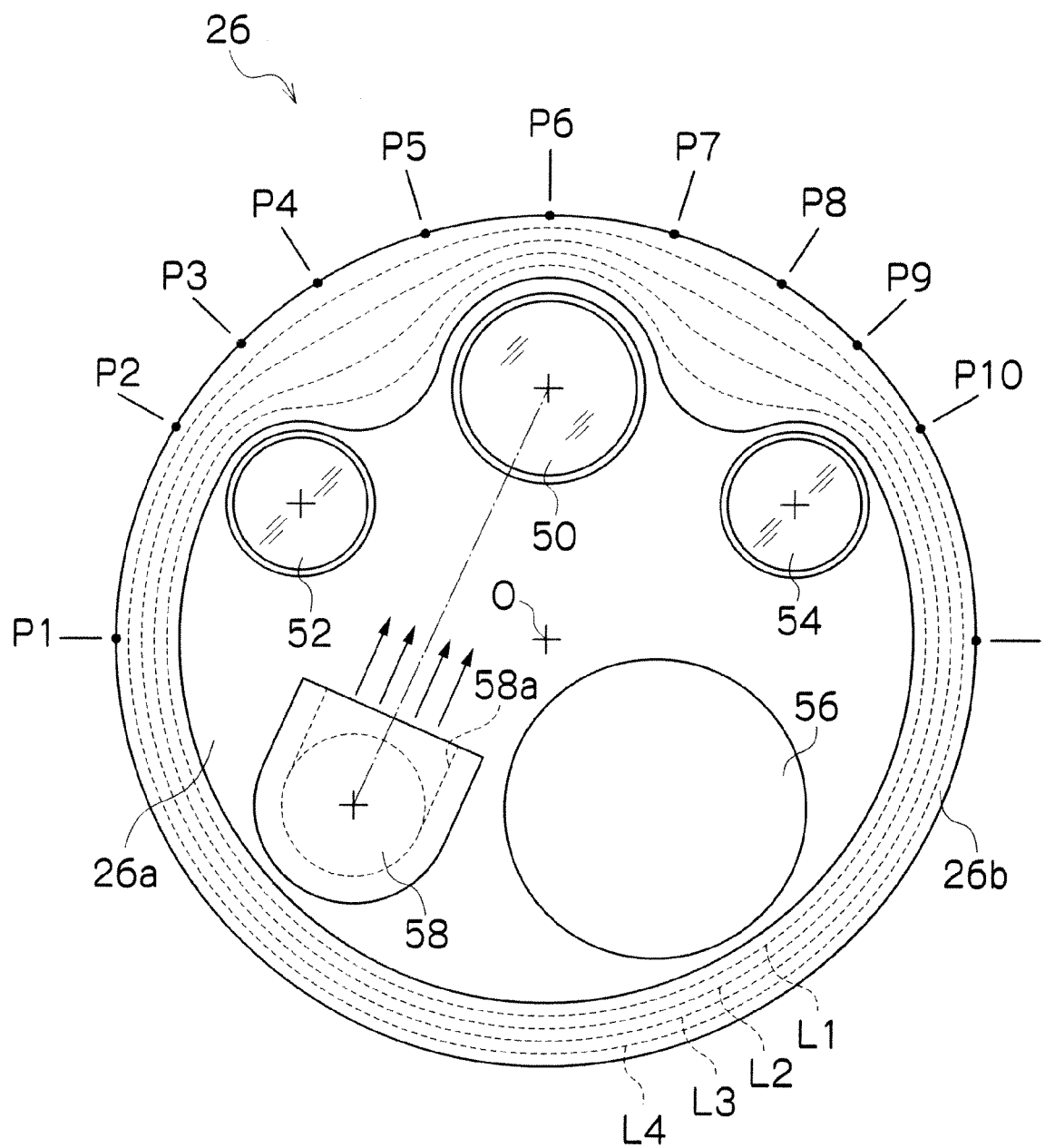
FIG. 2 is a front view illustrating a configuration of a distal end surface of a distal end part.

FIG. 2 is a front view illustrating a configuration of a distal end surface of the distal end part. As illustrated in FIG. 2, a distal end surface 26a of the distal end part 26 included in the insertion part 20 is formed into a flat circular shape, and the observation window 50, a pair of illumination windows 52 and 54, the forceps exit 56, and the nozzle 58 are placed on the distal end surface 26a. Particularly, in the endoscope 1 of the present embodiment, the observation window 50 is placed in the vicinity of a peripheral edge part 26b of the distal end surface 26a, and the pair of illumination windows 52 and 54 is placed in the vicinity of the peripheral edge part 26b adjacently to the observation window 50 so as to sandwich the observation window 50. In addition, the nozzle 58 is placed so as to be opposed to the observation window 50, and the forceps exit 56 is placed adjacently to the nozzle 58.

In addition, in the endoscope 1 of the present embodiment, in order to reduce a stimulus when the distal end part 26 comes into contact with a body cavity wall, an entire circumference of the peripheral edge part 26b of the distal end surface 26a is round-chamfered.

It should be noted that, if the peripheral edge part 26b is round-chamfered in this way, liquid drops attach more easily onto the peripheral edge part 26b, so that the liquid drops attach more easily onto the vicinities of the observation window 50 and the illumination windows 52 and 54.

In view of the above, in the endoscope 1 of the present embodiment, a radius of curvature (round-chamfer) of the peripheral edge part 26b is changed in the vicinities of the observation window 50 and the illumination windows 52 and 54, to thereby prevent the liquid drops from attaching onto the vicinities of optical members such as the observation window 50 and the illumination windows 52 and 54. This will be described in detail later.

An objective optical system such as an objective lens is attached behind the observation window 50, and a solid-state image pick-up element (for example, CCD (Charge Coupled Device)) is attached further behind the objective optical system.

In addition, an illumination optical system is placed behind each of the paired illumination windows 52 and 54.

A light guide (not shown) provided inside of the insertion part 20 is connected to the illumination optical system. When the light source connector 34B of the connection part 30 is connected to the light source apparatus 38, this light guide is connected to a light source lamp (not shown) incorporated in the light source apparatus 38. Accordingly, when the light source lamp of the light source apparatus 38 is turned on, light emitted from the light source lamp is guided by the light guide to the illumination optical systems. Then, the lights guided by the illumination optical systems illuminate a region to be observed through the illumination windows 52 and 54.

The objective optical system placed behind the observation window 50 receives reflected light of the light which illuminates the region to be observed through the illumination windows 52 and 54, and forms an optical image of the region to be observed on a light receiving surface of the solid-state image pick-up element. The optical image of the region to be observed which is formed on the light receiving surface of the solid-state image pick-up element is converted into an electrical signal by the solid-state image pick-up element, and is outputted to the processor apparatus 36 which is connected to the endoscope 1 via a signal line (not shown) provided inside of the insertion part 20. The processor apparatus 36 converts this electrical signal into a video signal, and outputs the video signal as an endoscopic image to the monitor 42.

The forceps exit 56 is connected to the forceps entrance 12 of the operation part 10 via a forceps channel (not shown) provided inside of the insertion part 20. A treatment tool such as a forceps which is inserted from the forceps entrance 12 protrudes from the forceps exit 56.

The nozzle 58 is provided so as to protrude from the distal end surface 26a of the distal end part 26, and includes a jet port 58a facing the observation window 50. An air supply/water supply channel (not shown) provided inside of the insertion part 20 is connected to the nozzle 58. The air supply/water supply channel is connected to the air supply/water supply apparatus 40 via the air supply/water supply connector 34C of the connection part 30. When the air supply/water supply button 16 provided in the operation part 10 is operated, air or water (cleaning fluid) is selectively fed from the air supply/water supply apparatus 40 to the endoscope 1 via the air supply/water supply channel. Then, the air or the water fed from the air supply/water supply apparatus 40 is fed to the nozzle 58 via the air supply/water supply channel to be jetted from the jet port 58a of the nozzle 58 toward the observation window 50. This enables cleaning of the observation window 50.

It should be noted that the observation window 50 is cleaned by jetting water from the nozzle 58. In this case, drops of water may attach onto the observation window 50 after the cleaning. Therefore, after the cleaning, air is jetted from the nozzle 58, to thereby remove the drops of water attaching on the observation window 50.

However, as in the endoscope 1 of the present embodiment, if the observation window 50 is placed in the vicinity of the peripheral edge part 26b and the peripheral edge part 26b is round-chamfered, the liquid drops attach more easily onto the peripheral edge part 26b in the vicinity of the observation window 50. In addition, if the liquid drops attach onto the peripheral edge part 26b, the liquid drops cannot be removed in some cases even by jetting air thereto.

In view of the above, in the endoscope 1 of the present embodiment, the radius of curvature (round-chamfer) of the peripheral edge part 26b is changed in the vicinities of the observation window 50 as well as the illumination windows 52 and 54, to thereby prevent the liquid drops from attaching onto the vicinities of the optical members such as the observation window 50 and the illumination windows 52 and 54. That is, the liquid drops tend to attach more easily onto a portion having a larger radius of curvature (round-chamfer), and hence the radius of curvature is changed in the vicinities of the observation window 50 and the respective illumination windows 52 and 54, to thereby cause the liquid drops to attach at a position far from the observation window 50 and the illumination windows 52 and 54. Specifically, as illustrated in FIG. 2, the peripheral edge part 26b in the vicinities of the observation window 50 and the illumination windows 52 and 54 is round-chamfered in a manner that the radius of curvature (round-chamfer) becomes larger in portions between the observation window 50 and the respective illumination windows 52 and 54. Hereinafter, description is given of modes for round-chamfering the peripheral edge part 26b in the vicinities of the observation window 50 and the illumination windows 52 and 54.

In FIG. 2, broken lines L1 to L4 in the peripheral edge part 26b each designate a contour line.

As illustrated in FIG. 2, in a peripheral edge part between the observation window 50 and the illumination window 52 (a peripheral edge part having a shorter circumferential length), a point (P6) closest to the observation window 50 is defined as the first point, a point (P2) closest to the illumination window 52 is defined as the second point, and a point (P4) between the first point and the second point is defined as the local maximum point (a point at which the radius of curvature (round-chamfer) becomes the largest). Then, this peripheral edge part is round-chamfered in a manner that the radius of curvature (round-chamfer) gradually becomes larger from each of the first point (P6) and the second point (P2) toward the local maximum point (P4).

Similarly, in a peripheral edge part between the observation window 50 and the illumination window 54 (a peripheral edge part having a shorter circumferential length), the point (P6) closest to the observation window 50 is defined as the first point, a point (P10) closest to the illumination window 54 is defined as the second point, and a point (P8) between the first point and the second point is defined as the local maximum point. Then, this peripheral edge part is round-chamfered in a manner that the radius of curvature (round-chamfer) gradually becomes larger from each of the first point (P6) and the second point (P10) toward the local maximum point (P8).

In the endoscope 1 of the present embodiment, the local maximum point (P4, P8) is set at a substantially intermediate position between the first point (P6) and the second point (P2, P10), and the radius of curvature (round-chamfer) becomes the largest at a point having substantially the same distance from both of the first point (P6) and the second point (P2, P10).

Figure 3A:
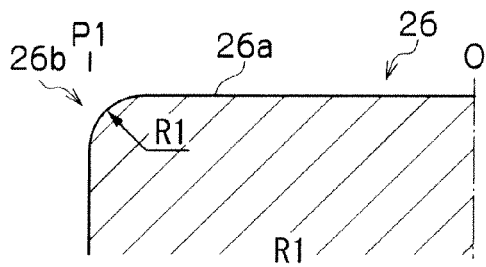
FIGS. 3A to 3J are views each illustrating an outer shape of a given cross section of the distal end part illustrated in FIG. 2.
Figure 3B:
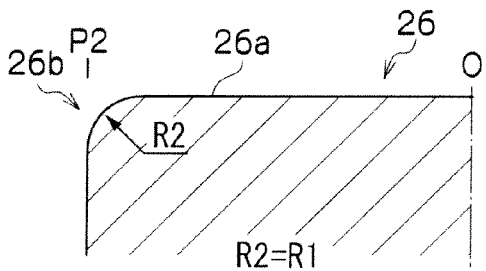
Figure 3C:
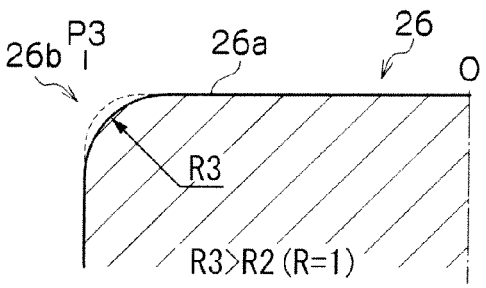
Figure 3D:
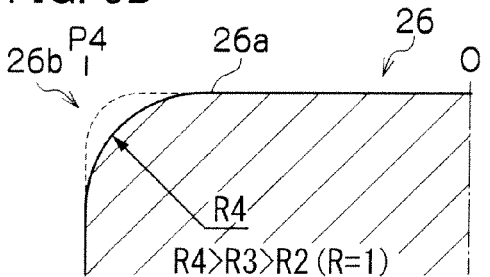
Figure 3E:
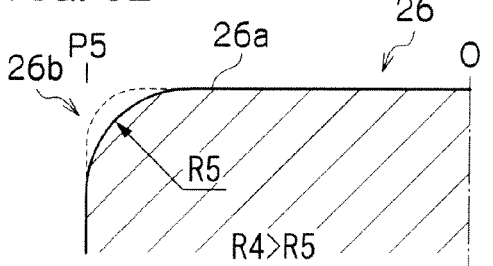
Figure 3F:
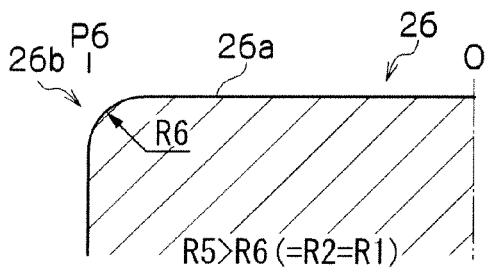
Figure 3G:
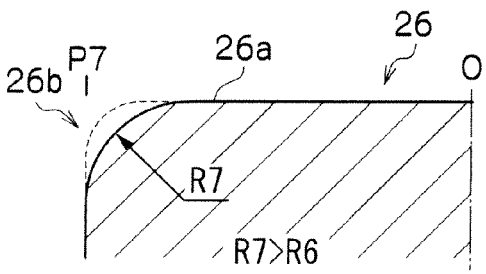
Figure 3H:
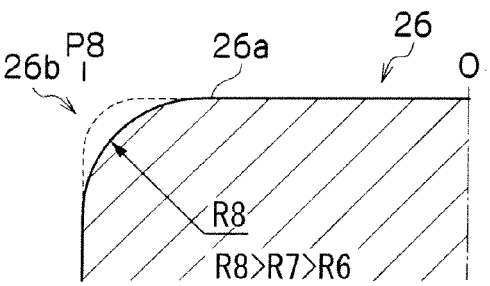
Figure 3I:
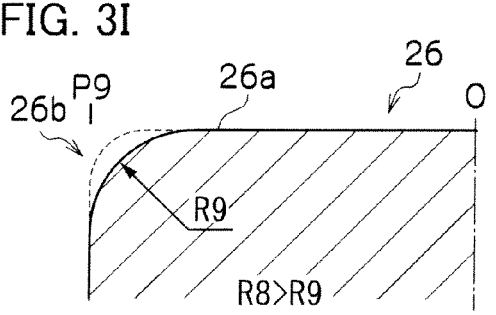
Figure 3J:
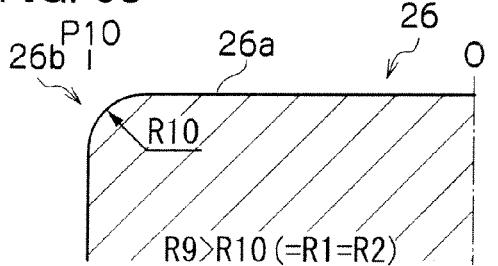

FIGS. 3A to 3J are views each illustrating an outer shape of a given cross section of the distal end part illustrated in FIG. 2. FIG. 3A illustrates the outer shape of an O-P1 cross section in FIG. 2, FIG. 3B illustrates the outer shape of an O-P2 cross section in FIG. 2, FIG. 3C illustrates the outer shape of an O-P3 cross section in FIG. 2, FIG. 3D illustrates the outer shape of an O-P4 cross section in FIG. 2, FIG. 3E illustrates the outer shape of an O-P5 cross section in FIG. 2, FIG. 3F illustrates the outer shape of an O-P6 cross section in FIG. 2, FIG. 3G illustrates the outer shape of an O-P7 cross section in FIG. 2, FIG. 3H illustrates the outer shape of an O-P8 cross section in FIG. 2, FIG. 3I illustrates the outer shape of an O-P9 cross section in FIG. 2, and FIG. 3J illustrates the outer shape of an O-P10 cross section in FIG. 2.

In FIG. 2, a point O is the center of the distal end surface 26a, the point P6 is the point closest to the observation window 50, the point P2 is the point closest to the illumination window 52, the point P10 is the point closest to the illumination window 54, the point P4 is the local maximum point set between the point P2 and the point P6, and the point P8 is the local maximum point set between the point P6 and the point P10.

As illustrated in FIGS. 3A to 3J, the distal end part in the vicinity of the observation window 50 is round-chamfered in the following manner. That is, taking a point (P6) closest to the observation window 50 as a starting point, the radius of curvature (round-chamfer) gradually becomes larger along with an increase in distance from the observation window 50 toward the respective illumination windows 52 and 54. Then, the radius of curvature becomes the local maximum at the local maximum points (P4, P8) set between the observation window 50 and the respective illumination windows 52 and 54.

Similarly, the distal end part in the vicinities of the illumination windows 52 and 54 is round-chamfered in the following manner. That is, taking points (P2, P10) closest to the respective illumination windows 52 and 54 as starting points, the radius of curvature (round-chamber) gradually becomes larger along with an increase in distance from the respective illumination windows 52 and 54 toward the observation window 50. Then, the radius of curvature becomes the local maximum (for example, 1.5 mm at maximum) at the local maximum points (P4, P8) set between the observation window 50 and the respective illumination windows 52 and 54.

In this way, the radius of curvature (round-chamfer) at the peripheral edge part 26b of the distal end surface 26a is changed in the vicinities of the observation window 50 and the illumination windows 52 and 54, whereby it is possible to prevent the liquid drops from attaching onto the vicinities of the observation window 50 and the illumination windows 52 and 54 and to secure an excellent field of view.

Particularly, as in the endoscope 1 of the present embodiment, taking the points respectively closest to the observation window 50 and the illumination windows 52 and 54 as the starting points, the distal end part is round-chamfered in a manner that the radius of curvature (round-chamfer) gradually becomes larger, whereby it is possible to lead the liquid drops to a position away from the observation window 50 and the illumination windows 52 and 54 and to prevent the liquid drops from attaching onto the vicinities of the observation window 50 and the illumination windows 52 and 54.

The radius of curvature (round-chamfer) is changed in the vicinity of the observation window 50, and the range of this vicinity may be defined as, for example, a region which is sandwiched by two tangents drawn from the center O of the distal end surface 26a to the observation window 50. In addition, in the case where the radius of curvature is changed also in the vicinities of the illumination windows 52 and 54, the range thereof may be defined as a region which is sandwiched by two tangents drawn from the center O of the distal end surface 26a to each of the illumination windows 52 and 54.

In addition, the presently disclosed subject matter provides a technology which is effective when the observation window 50 and the illumination windows 52 and 54 are placed in the vicinity of the peripheral edge part of the distal end surface 26a, and is particularly effective when a central position of the observation window 50 or the illumination windows 52 and 54 is located on the outer side of ½ the radius of the distal end surface 26a (when a distance from the center O of the distal end surface 26a to the outer periphery is assumed as r and the central position of the observation window 50 or the illumination windows 52 and 54 is located on the outer side of a distance position of 0.5×r from the center O of the distal end surface 26a).

In addition, in the present embodiment, the radius of curvature (round-chamfer) is continuously changed with respect to the point closest to the observation window 50 as the starting point, but a mode of changing the radius of curvature is not limited thereto. In addition to this mode, for example, the radius of curvature may be changed in a stepwise manner. In addition, a change rate for changing the radius of curvature does not necessarily need to be constant, and may be changed drastically with respect to a certain point as the starting point. For example, it is also possible to adopt a mode in which: the point closest to the observation window 50 is defined as the starting point; and the distal end part is round-chamfered at the same radius of curvature as that at the starting point within a given range from the starting point, and is round-chamfered at a radius of curvature which is changed continuously or in a stepwise manner, once exceeding a given range (in this case, both ends of the given range including the starting point correspond to actual starting points). The same holds true for the case where the radius of curvature is changed in the vicinities of the illumination windows 52 and 54.

Second Embodiment

Figure 4:
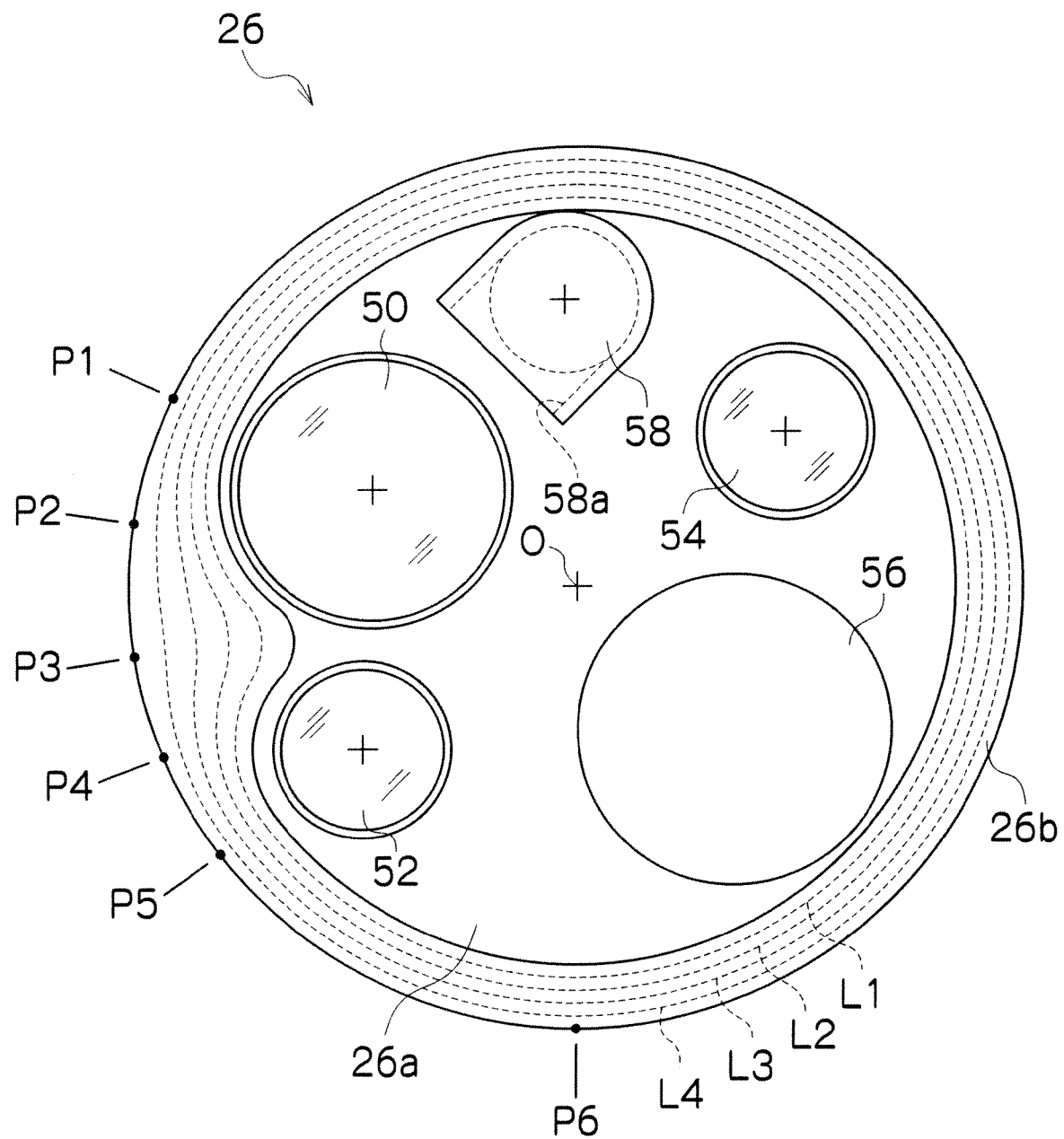
FIG. 4 is a front view illustrating a configuration of a second embodiment of the distal end surface of the distal end part.

FIG. 4 is a front view illustrating a configuration of a second embodiment of the distal end surface of the distal end part of the endoscope according to the presently disclosed subject matter.

The endoscope of the present embodiment is different in the layout of each constituent element placed on the distal end surface of the distal end part from the endoscope of the first embodiment. That is, in the layout of the endoscope 1 of the first embodiment, the pair of illumination windows 52 and 54 is placed in the vicinity of the peripheral edge part 26b so as to sandwich the observation window 50. On the other hand, in the layout of the endoscope of the present embodiment, the observation window 50 is placed in the vicinity of one illumination window 52, and the nozzle 58 is placed between the other illumination window 54 and the observation window 50.

The endoscope of the present embodiment is the same as the endoscope of the first embodiment in that: the observation window 50 and the illumination windows 52 and 54 are placed in the vicinity of the peripheral edge part 26b; and the nozzle 58 is placed so as to be opposed to the observation window 50.

As illustrated in FIG. 4, similarly in the endoscope of the present embodiment, the radius of curvature (round-chamfer)

of the peripheral edge part 26b is changed in the vicinity of the observation window 50, to thereby prevent the liquid drops from attaching onto the vicinity of the observation window 50.

In FIG. 4, broken lines L1 to L4 in the peripheral edge part 26b each designate a contour line. As illustrated in FIG. 4, in a peripheral edge part between the observation window 50 and the illumination window 52 (a peripheral edge part having a shorter circumferential length), a point (P1) closest to the observation window 50 is defined as the first point, a point (P5) closest to the illumination window 52 is defined as the second point, and a point (P3) between the first point and the second point is defined as the local maximum point. Then, this peripheral edge part is round-chamfered in a manner that the radius of curvature (round-chamfer) gradually becomes larger from each of the first point (P1) and the second point (P5) toward the local maximum point (P3).

Figure 5A:
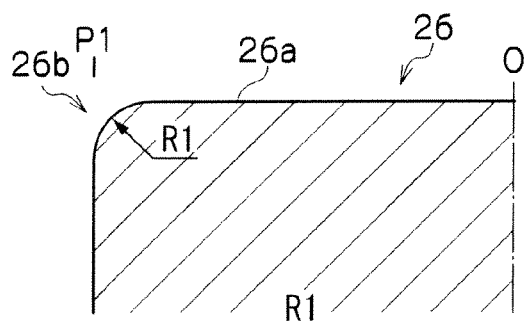
FIGS. 5A to 5F are views each illustrating an outer shape of a given cross section of the distal end part illustrated in FIG. 4.
Figure 5D:
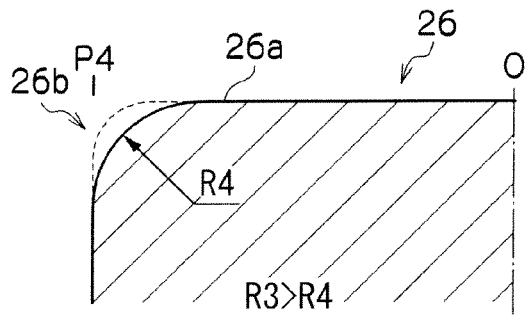
Figure 5B:
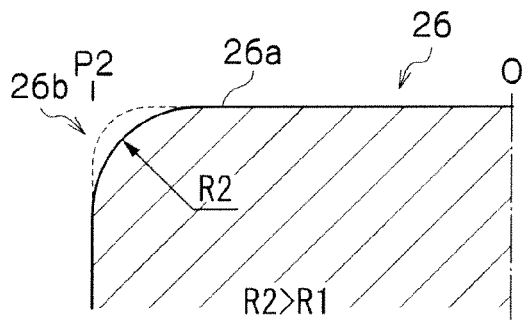
Figure 5E:
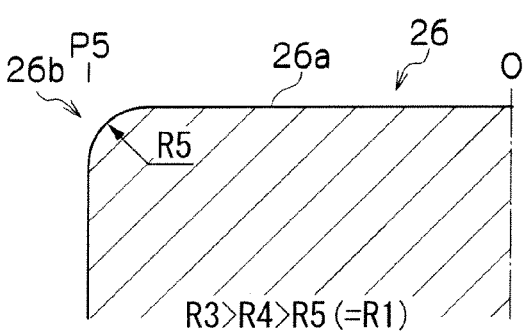
Figure 5C:
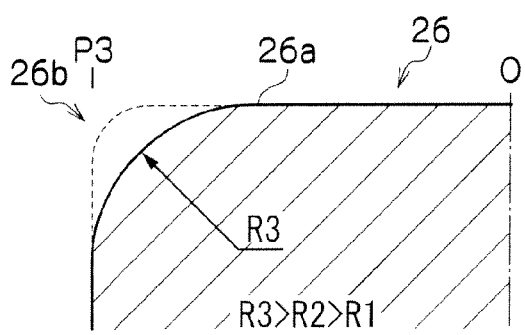
Figure 5F:
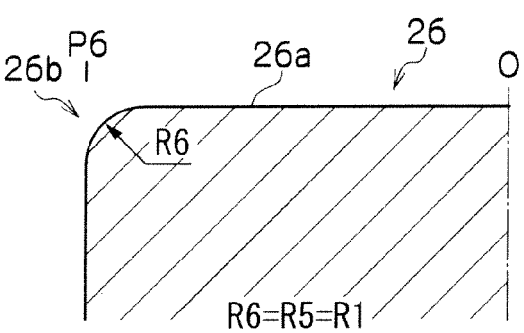

FIGS. 5A to 5F are views each illustrating an outer shape of a given cross section of the distal end part illustrated in FIG. 4. FIG. 5A illustrates the outer shape of an O-P1 cross section in FIG. 4, FIG. 5B illustrates the outer shape of an O-P2 cross section in FIG. 4, FIG. 5C illustrates the outer shape of an O-P3 cross section in FIG. 4, FIG. 5D illustrates the outer shape of an O-P4 cross section in FIG. 4, FIG. 5E illustrates the outer shape of an O-P5 cross section in FIG. 4, and FIG. 5F illustrates the outer shape of an O-P6 cross section in FIG. 4.

In FIG. 4, the point O is the center of the distal end surface 26a, the point P1 is the point closest to the observation window 50, the point P5 is the point closest to the illumination window 52, and the point P3 is the local maximum point set between the point P1 and the point P5.

As illustrated in FIGS. 5A to 5F, the peripheral edge part between the observation window 50 and the illumination window 52 is round-chamfered in a manner that the radius of curvature (round-chamfer) gradually becomes larger from each of the point (P1) closest to the observation window 50 and the point (P5) closest to the illumination window 52 toward the local maximum point (P3).

In this way, the radius of curvature (round-chamfer) of the peripheral edge part 26b is changed in the vicinity of the observation window 50, whereby it is possible to prevent the liquid drops from attaching onto the vicinities of the observation window 50 and the illumination window 52 placed in the vicinity of the observation window 50 and to secure an excellent field of view.

Figure 6:
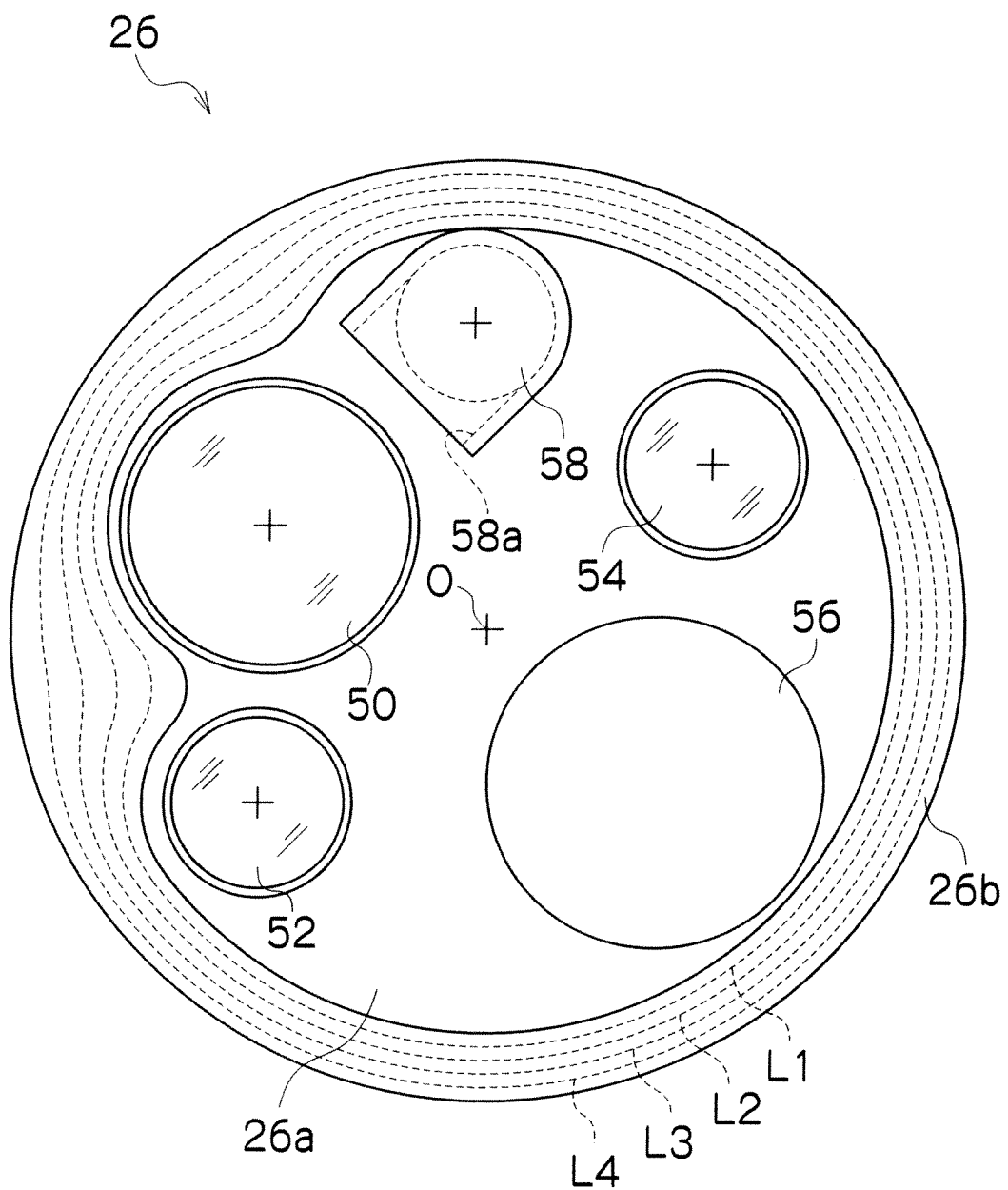
FIG. 6 is a front view illustrating a configuration of another embodiment of the distal end surface of the distal end part.

Although, in the endoscope illustrated in FIG. 4, the radius of curvature (round-chamfer) of the peripheral edge part 26b is changed toward one direction (toward the illumination window 52) with taking the point closest to the observation window 50 as the starting point, alternatively, as illustrated in FIG. 6, the radius of curvature (round-chamfer) may be changed toward two directions.

In addition, as the cleaning fluid jetted from the nozzle 58 advances to the downstream side, a flow rate thereof becomes lower, so that the cleaning fluid attaches more easily onto the distal end surface 26a and the peripheral edge part 26b. Therefore, it is preferable to actively change the radius of curvature (round-chamfer) of the peripheral edge part 26b which is located on the downstream side of the observation window 50 with respect to the nozzle 58. That is, the flow rate is high in a region on the upstream side of the observation window 50 with respect to the nozzle 58 (a region near the nozzle 58), and hence the liquid drops are less likely to attach thereonto. Therefore, it is possible to prevent the liquid drops from attaching in the region on the upstream side, even without actively changing the radius of curvature (round-chamfer).

Third Embodiment

Figure 7:
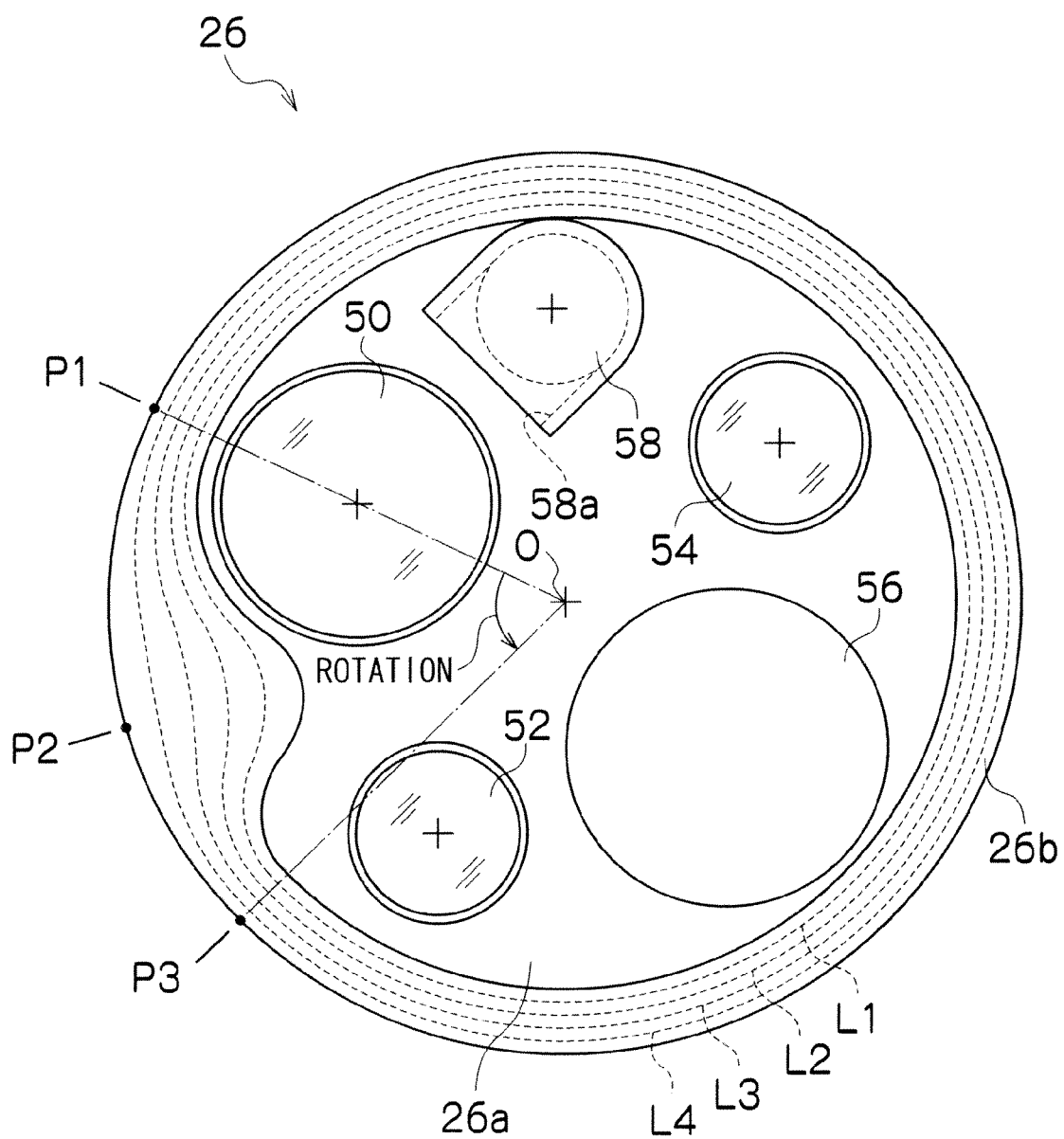
FIG. 7 is a front view illustrating a configuration of a third embodiment of the distal end surface of the distal end part.

FIG. 7 is a front view illustrating a configuration of a third embodiment of the distal end surface of the distal end part of the endoscope according to the presently disclosed subject matter.

The endoscope of the present embodiment is different in the layout of each constituent element placed on the distal end surface of the distal end part from the endoscope of the first embodiment. That is, in the endoscope of the present embodiment, the illumination window 52 is placed at a position a little away from the observation window 50.

In this case, as illustrated in FIG. 7, in a peripheral edge part in the vicinity of the observation window 50, a point (P1) closest to the observation window 50 is taken as the starting point, and a point (P3) obtained by rotating the distal end part 26 by a given angle from the starting point around the point O in one direction, is taken as the ending point. Then, a local maximum point (P2) is set between the starting point and the ending point. This peripheral edge part is round-chamfered in a manner that the radius of curvature (round-chamfer) gradually becomes larger from each of the starting point and the ending point toward the local maximum point and becomes the largest at the local maximum point.

In this way, in the case where the illumination windows 52 and 54 are not placed in the vicinity of the observation window 50, the point closest to the observation window 50 is taken as the starting point, and the point obtained by rotating the distal end part 26 by the given angle from the starting point around the point O in one direction, is taken as the ending point. Then, the radius of curvature (round-chamfer) of the peripheral edge part 26b is changed between the starting point and the ending point. This makes it possible to prevent the liquid drops from attaching onto the vicinity of the observation window 50 and to secure an excellent field of view.

Although, in the embodiment illustrated in FIG. 7, the radius of curvature (round-chamfer) of the peripheral edge part 26b is changed only on one side of the observation window 50, alternatively, the radius of curvature may be changed on both sides of the observation window 50 (see FIG. 6). In this case, the radius of curvature does not necessarily need to be symmetrically changed, and it is preferable to change the radius of curvature in consideration of the layout of another constituent member, a distance from the nozzle, and the like.

In addition, in the case where the radius of curvature (round-chamfer) is changed on one side of the observation window 50, it is preferable to take, as the ending point, a point obtained by rotating the distal end part 26 around the point O by a given angle in a direction away from the nozzle 58 (toward the downstream side of the cleaning fluid jetted from the nozzle 58).

In addition, although, in the embodiment illustrated in FIG. 7, the radius of curvature (round-chamfer) is not changed in peripheral edge parts in the vicinities of the illumination windows 52 and 54, it may be changed also in the peripheral edge parts in the vicinities of the illumination windows 52 and 54.

Fourth Embodiment

Figure 8:
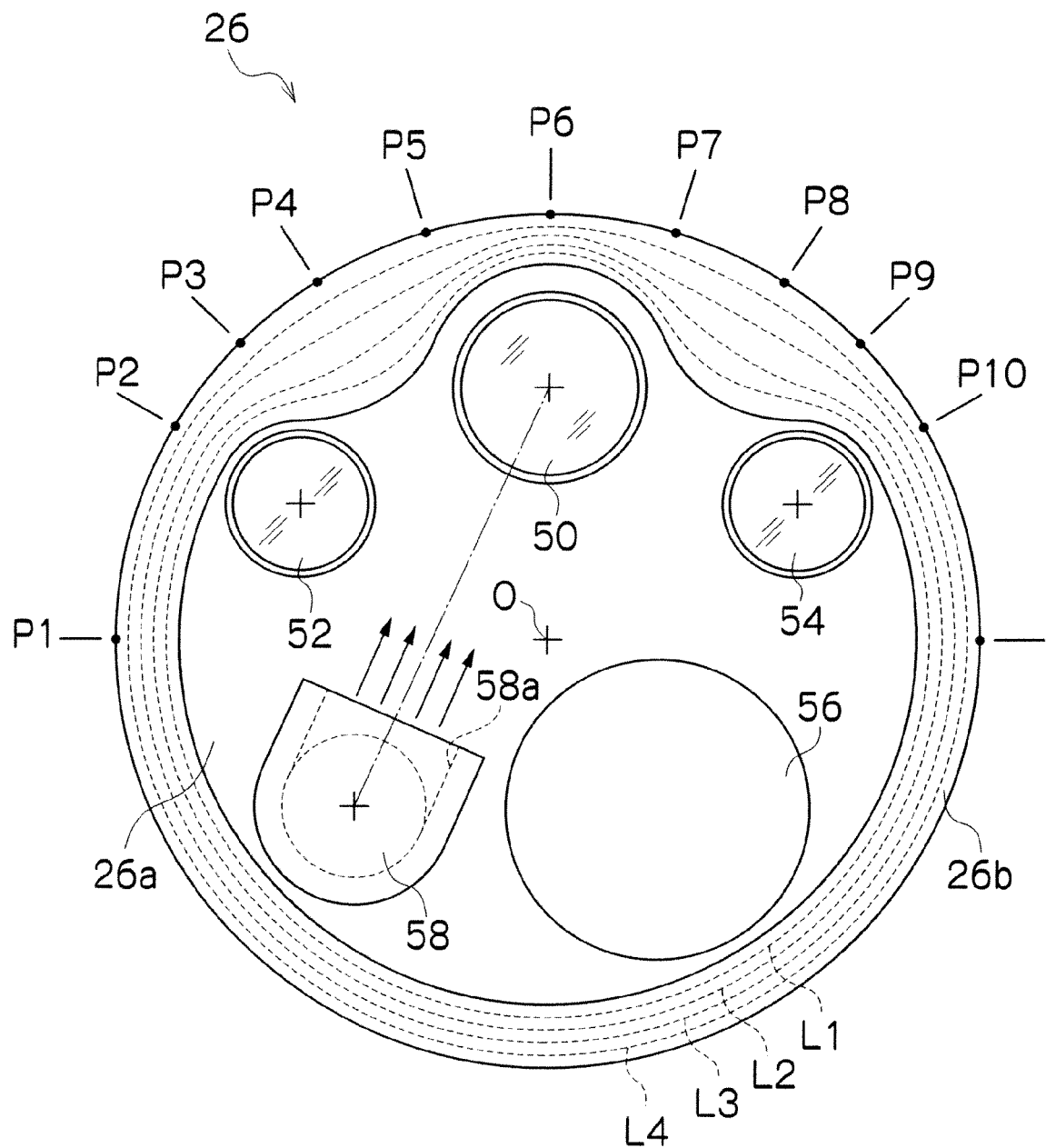
FIG. 8 is a front view illustrating a configuration of a fourth embodiment of the distal end surface of the distal end part.

FIG. 8 is a front view illustrating a configuration of a fourth embodiment of the distal end surface of the distal end part of the endoscope according to the presently disclosed subject matter.

Figure 9A:
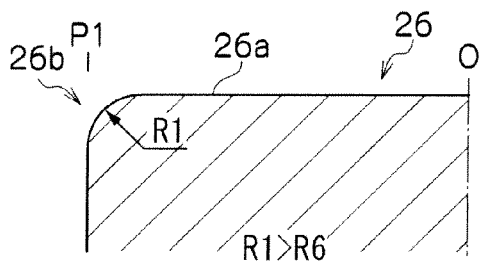
FIGS. 9A to 9J are views each illustrating an outer shape of a given cross section of the distal end part illustrated in FIG. 8.
Figure 9B:
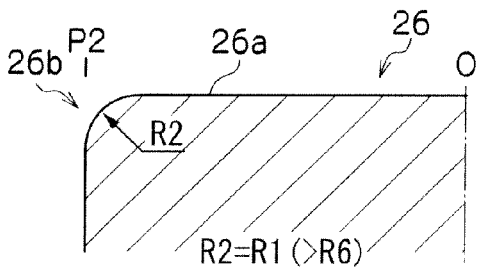
Figure 9C:
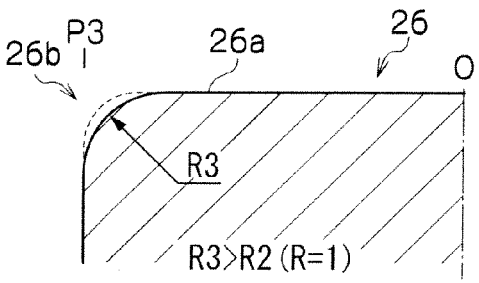
Figure 9D:
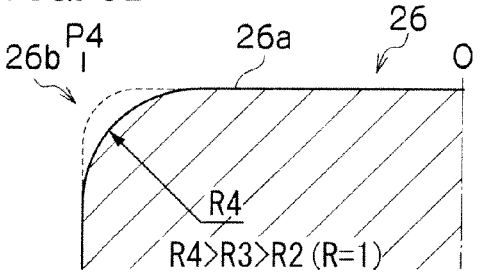
Figure 9E:
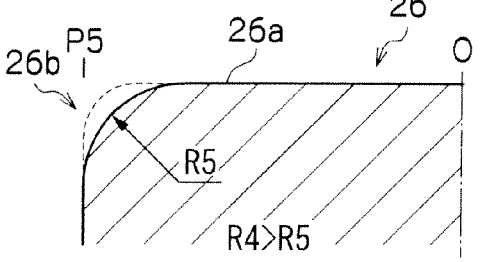
Figure 9F:
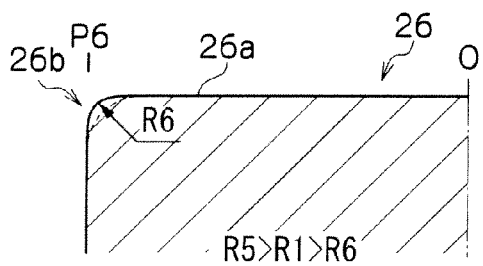
Figure 9G:
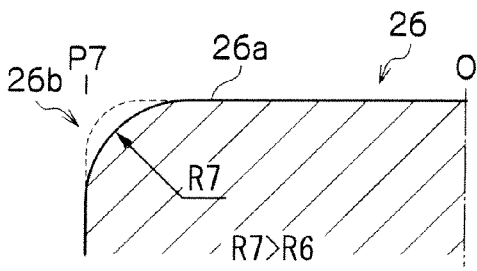
Figure 9H:
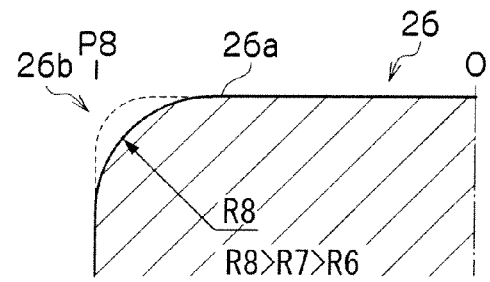
Figure 9I:
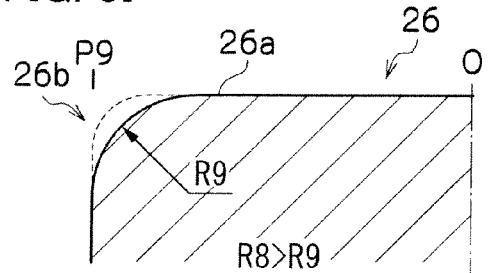
Figure 9J:
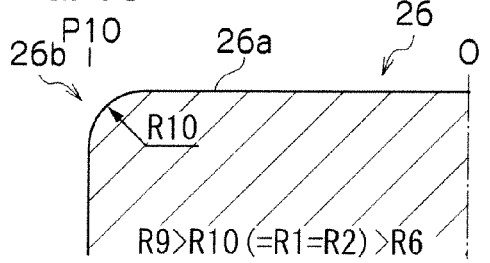

In addition, FIGS. 9A to 9J are views each illustrating an outer shape of a given cross section of the distal end part illustrated in FIG. 8. FIG. 9A illustrates the outer shape of an O-P1 cross section in FIG. 8, FIG. 9B illustrates the outer shape of an O-P2 cross section in FIG. 8, FIG. 9C illustrates the outer shape of an O-P3 cross section in FIG. 8, FIG. 9D illustrates the outer shape of an O-P4 cross section in FIG. 8, FIG. 9E illustrates the outer shape of an O-P5 cross section in FIG. 8, FIG. 9F illustrates the outer shape of an O-P6 cross section in FIG. 8, FIG. 9G illustrates the outer shape of an O-P7 cross section in FIG. 8, FIG. 9H illustrates the outer shape of an O-P8 cross section in FIG. 8, FIG. 9I illustrates the outer shape of an O-P9 cross section in FIG. 8, and FIG. 9J illustrates the outer shape of an O-P10 cross section in FIG. 8.

As illustrated in FIG. 8 and FIGS. 9A to 9J, the endoscope of the present embodiment is different from the endoscope of the first embodiment in that the peripheral edge part 26b is round-chamfered in a manner that a radius of curvature (round-chamfer) (R6) at the point (P6) closest to the observation window 50 becomes the smallest.

That is, in the endoscope of the first embodiment, the radius of curvature (R6) at the point (P6) closest to the observation window 50 is set to the same radius of curvature as a radius of curvature of a portion other than the vicinity of the observation window 50 (for example, the radius of curvature at the point P1). On the other hand, in the endoscope of the present embodiment, the radius of curvature at the point (P6) closest to the observation window 50 is set to be the smallest, and the peripheral edge part 26b is chamfered in a manner that the radius of curvature gradually becomes larger along with an increase in distance from the point (P6) closest to the observation window 50 (for example, the smallest radius of curvature is approximately 0.5 mm, and the largest radius of curvature is approximately 1.5 mm).

As described above, because the liquid drops tend to attach more easily onto a portion having a larger radius of curvature (round-chamfer), the radius of curvature at the point closest to the observation window 50 is set to be the smallest in the embodiments. This enables to more effectively prevent the liquid drops from attaching onto the observation window 50.

Similarly with regard to the illumination windows 52 and 54, the radius of curvature at the point closest to each of the illumination windows 52 and 54 is made smaller, whereby it is possible to more effectively prevent the liquid drops from attaching onto the illumination windows 52 and 54.

What is claimed is:

1. An endoscope comprising:
an insertion part which is inserted into a body cavity, the insertion part having:
a flat distal end surface, the flat distal end surface including an observation window, an illumination window, an outer peripheral edge, and a nozzle which jets a cleaning fluid toward the observation window;
an outer circumferential surface centered along a longitudinal axis of the insertion part; and
a chamfered surface disposed between the outer peripheral edge and the outer circumferential surface and being circumferentially round-chamfered,
wherein a center O of the flat distal end surface lies on the longitudinal axis of the insertion part,
wherein a distance between the center O of the flat distal end surface and the outer peripheral edge is assumed as r,
wherein the observation window is located in a vicinity of the outer peripheral edge and a central position of the observation window is located on an outer side of a distance position of 0.5×r from the center O of the flat distal end surface, and
wherein in a vicinity of the observation window which is a region sandwiched by two tangents drawn from the center O of the flat distal end surface to the observation window, the chamfered surface is round-chamfered in a manner that as a distance between a central axis of the observation window and a point of a plurality of points along the outer circumferential surface increases, a radius of round-chamfer of the chamfered surface increases.

2. The endoscope according to claim 1, wherein:
the illumination window is located in the vicinity of the outer peripheral edge, a central position of the illumination window is located on the outer side of the distance position of 0.5×r from the center O of the flat distal end surface; and
in a vicinity of the illumination window which is a region sandwiched by two tangents drawn from the center O of the flat distal end surface to the illumination window, the chamfered surface is round-chamfered in a manner that as a distance between a central axis of the illumination window and a point of a plurality of points along the outer circumferential surface increases, a radius of round-chamfer of the chamfered surface increases.

3. The endoscope according to claim 1, wherein the chamfered surface is round-chamfered in a manner that the radius of round-chamfer becomes smallest at a point closest to the observation window.

4. The endoscope according to claim 1, wherein the radius of round-chamfer of the chamfered surface between the central axis of the observation window and each point of the plurality of points increases in a stepwise manner.

5. The endoscope according to claim 1, wherein the radius of round-chamfer of the chamfered surface between the central axis of the observation window and each point of the plurality of points increases at a constant rate.

* * * * *